US012678324B2

(12) United States Patent
Geller

(10) Patent No.: US 12,678,324 B2
(45) Date of Patent: Jul. 14, 2026

(54) TONGUE POSITIONING DEVICE

(71) Applicant: Geller Generations LLC, Atlanta, GA (US)

(72) Inventor: Christopher Geller, La Fayette, GA (US)

(73) Assignee: Geller Generations LLC, Atlanta, GA (US)

( * ) Notice: Subject to any disclaimer, the term of this patent is extended or adjusted under 35 U.S.C. 154(b) by 84 days.

(21) Appl. No.: 18/740,717

(22) Filed: Jun. 12, 2024

(65) Prior Publication Data

US 2025/0381061 A1     Dec. 18, 2025

(51) Int. Cl.
*A61F 5/56* (2006.01)

(52) U.S. Cl.
CPC .................................... *A61F 5/566* (2013.01)

(58) Field of Classification Search
CPC .. A61F 5/56–566; A61B 13/00; A61M 16/04; A61M 16/0488–0495
See application file for complete search history.

(56) References Cited

U.S. PATENT DOCUMENTS

| | | | | |
|---|---|---|---|---|
| 3,809,094 | A | | 5/1974 | Cook |
| 4,198,967 | A | | 4/1980 | Dror |
| 4,520,813 | A | * | 6/1985 | Young .................... A61M 25/02 24/DIG. 42 |
| 6,679,901 | B1 | | 1/2004 | Takuma |
| 2004/0134490 | A1 | * | 7/2004 | Robertson ................. A61F 5/56 128/200.24 |
| 2014/0041673 | A1 | * | 2/2014 | Walters ............. A61M 16/0488 128/887 |
| 2020/0046545 | A1 | * | 2/2020 | Usman .................... A61F 5/566 |

FOREIGN PATENT DOCUMENTS

| | | | | |
|---|---|---|---|---|
| WO | WO-2008036787 A1 | * | 3/2008 | ........... A61K 33/244 |
| WO | WO-2014036668 A1 | * | 3/2014 | ............. A61F 5/566 |

OTHER PUBLICATIONS

Brand: Orofacial Myofunctional Therapy; Title: "Tongue Exercise—Tongue Pull-Ups" Link: https://innovativemyo.com/lesson-category/tongue-exercises/.
Brand: Bondesque; Title: "Stick Your Tongue out Mouth Gag" Link: https://www.bondesque.com/stick-your-tongue-out-mouth-gag.html?id=73296892.
Brand: SpeechGears; Title: "Tongue Depressor Sterilizable Shiny Stiff Soft Transparent Tongue Depressor Spatula" Link: https://www.indiamart.com/proddetail/tongue-depressor-sterilizable-shiny-stiff-soft-transparent-tongue-depressor-spatula-2852163211297.html.
Author: "CS Mott Children's Hospital"; Title: "Popsicle Harmonica" Link: https://www.mottchildren.org/posts/camp-little-victors/popsicle-harmonica.

* cited by examiner

*Primary Examiner* — Michelle J Lee
(74) *Attorney, Agent, or Firm* — Jeremy A. Briggs

(57) ABSTRACT

A tongue holding device is disclosed. The device may include a first elongated plate having a first proximal end and a first distal end, and a second elongated plate placed above the first elongated plate. The second elongated plate may include a second proximal end and a second distal end. The device may further include a first spacer and a second spacer. The first spacer may attach the first proximal end with the second proximal end and the second spacer may attach the first distal end with the second distal end. The first spacer and the second spacer may be further configured to form an opening between the first elongated plate and the second elongated plate at a middle portion of the first elongated plate and the second elongated plate. The opening may be configured to receive the user's tongue.

20 Claims, 5 Drawing Sheets

TONGUE POSITIONING DEVICE

TECHNICAL FIELD

The present disclosure relates to a tongue positioning device, and more specifically to a tongue positioning device that holds/retains a user's tongue in a forward position when the user sleeps.

BACKGROUND

Snoring affects hundreds of millions of people globally. The Sleep Foundation estimates that in the USA, snoring affects over half of men, over a third of women and over a fourth of children. Snoring may have various negative effects on the snorers' health including excessive sleepiness during waking hours. Snoring may affect the quality of sleep of others sleeping nearby, reducing their quality of life and causing social distress with the snorers. Snoring may also be a symptom of obstructive sleep apnea and the primary means by which obstructive sleep apnea harms human health.

Obstructive sleep apnea is a sleeping disorder in which the sleeper's breathing is stopped repeatedly throughout the night. In this, the air pathways narrow/block as a result of muscle relaxation in throat and tongue. The disorder may cause restless sleep, difficulty falling asleep or insomnia, excessive sleepiness throughout the day including increased risk of accidents as well as health issues caused through physical stress.

There exist various methods/devices to treat sleep apnea, which includes surgery, positive airway pressure (PAP) machines, exercises, lifestyle changes and mouthpieces. Surgery involves reducing, reinforcing or electrically stimulating tissue around the airway or positioning the tongue forward using piercing and anchors. PAP machines pump air into the airway through the nose and/or mouth, thereby opening the airway with sufficient pressure. Lifestyle changes involve weight-loss, reducing alcohol and/or sedative consumption, avoiding allergens and reducing smoking. Mouthpieces act by retaining the mandible or tongue forward. The mandible may be held forward through attachments to teeth. The tongue may be held forward using piercing or suction to attach the tongue to a connecter with the connecter also attached to teeth, bone or to any of various items outside of the mouth.

However, the conventional devices/methods have limitations and may cause inconvenience to the user. For example, some treatment devices (e.g., PAP machines) are dependent on electricity, which may not be usable in some environments such as camping, commercial flying, riding (as a passenger in an automobile), or taking a spontaneous nap outdoors. Further, the conventional mouthpieces that penetrate tissue may involve significant discomfort and risk of infection. Furthermore, the mouthpieces that move the mandible forward may cause changes in bite and/or discomfort in mandibular joints and/or connective tissues.

Thus, there is a need for a system that may effectively treat snoring/sleep apnea, without using electricity and without causing inconvenience to the user.

It is with respect to these and other considerations that the disclosure made herein is presented.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
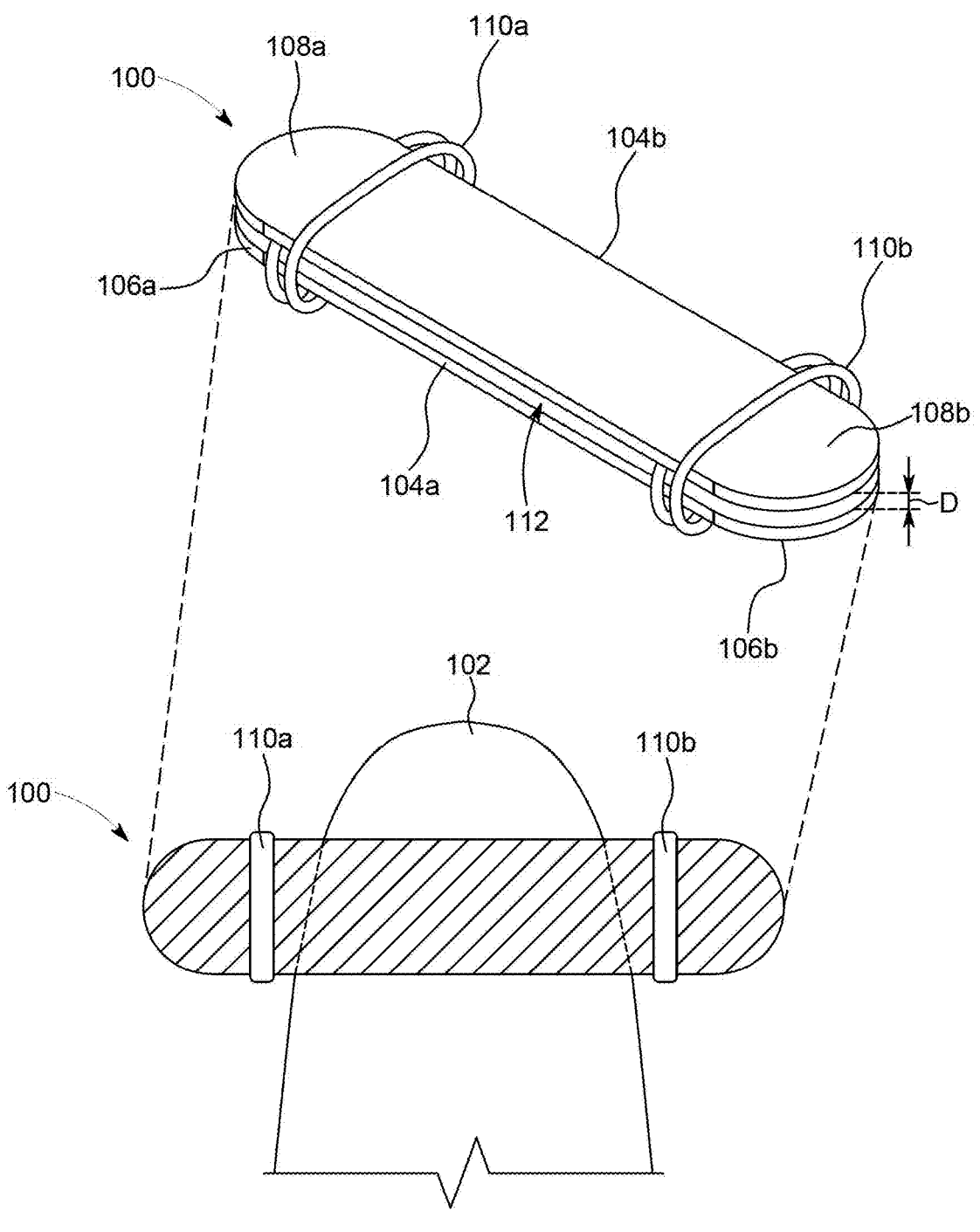
FIG. 1 depicts a first embodiment of a tongue positioning device in accordance with the present disclosure.

The present disclosure is directed to a tongue positioning device that is configured to hold a user's tongue in a forward direction or an extended position when the user sleeps. The device may be used by the user to treat snoring, sleep apnea, breathlessness, and/or the like. The device may include one or more elongated plates that may be disposed across the user's tongue, and rest against the commissures of the user's lips. In an exemplary aspect, the elongated plates may include a first elongated plate and a second elongated plate, which may be placed parallel to each other across the user's tongue. The second elongated plate may be disposed/placed at a predetermined distance away parallel from the first elongated plate, thus forming an opening that enables the user to insert the user's tongue between the first elongated plate and the second elongated plate.

In some aspects, the elongated plates may be rectangular plates with round edges. The elongated plates may be made of wood that may absorb water/saliva from the user's tongue, thereby creating a secure attachment to the user's tongue.

In some aspects, the first elongated plate and the second elongated plate may be held in place (or attached to each other) through an attachment mechanism or spacer(s). The spacers may be made of flexible material, and may include an elastic band or strap. The spacers may be positioned in proximity to proximal and distal ends of the first elongated plate and the second elongated plate, and may be configured to attach the proximal and distal ends of the first elongated plate and the second elongated plate. The spacers may attach the first elongated plate and the second elongated plate such that an opening may be formed between the first elongated plate and the second elongated plate at a middle portion of the first elongated plate and the second elongated plate. The opening enables the user to insert the user's tongue in the opening.

In further aspects, the device may include a cover that may cover/enclose the first elongated plate, the second elongated plate, and/or the spacers. In further aspects, the cover may cover a tip portion or the outermost portion of the user's tongue when the user wears the device to hold the user's tongue.

The present disclosure discloses a tongue positioning device that holds the user's tongue in the forward direction when the user sleeps, without causing any inconvenience to the user. The device may be used to treat snoring, sleep apnea, and/or the like, and does not depend on electricity. Further, the user is not required to undergo any surgery to use the device, and the device does not penetrate tissue and does not force mandibular movement. The device is easy to manufacture and easy to use. In addition, the cover prevents the user's tongue from getting dirty when the user sleeps with the device placed over the tongue.

These and other advantages of the present disclosure are provided in detail herein.

Illustrative Embodiments

The disclosure will be described more fully hereinafter with reference to the accompanying drawings, in which example embodiments of the disclosure are shown, and not intended to be limiting.

FIG. 1 depicts a first embodiment of a tongue positioning device 100 in accordance with the present disclosure. The tongue positioning device 100 (or device 100) may be configured to hold a user's tongue 102 in a forward position (or an "extended" position) when the user sleeps, which prevents slipping of the user's tongue 102 back towards the throat. The device 100 may be used to treat snoring/sleep apnea. A person ordinarily skilled in the art may appreciate that when the user's tongue 102 is held in the forward position or the extended position, the user may easily breathe while sleeping, thereby considerably reducing the probability of snoring or sleep apnea.

In some aspects, the device 100 may include a first elongated plate 104a (or a lower plate) and a second elongated plate 104b (or an upper plate), as shown in FIG. 1. The first elongated plate 104a may include a first proximal end 106a and a first distal end 106b. Similarly, the second elongated plate 104b may include a second proximal end 108a and a second distal end 108b. In some aspects, the second elongated plate 104b may be disposed/placed parallelly above the first elongated plate 104a, and at a predetermined distance "D" from the first elongated plate 104a, which enables the user to conveniently insert the user's tongue 102 between the first elongated plate 104a and the second elongated plate 104b. When the user inserts the user's tongue 102 between the first elongated plate 104a and the second elongated plate 104b, the second elongated plate 104b may adhere to a user's tongue 102 top surface and the first elongated plate 104a may adhere to a user's tongue 102 bottom surface. The first elongated plate 104a and the second elongated plate 104b may be held in place by hydrophilic adhesion or through any of various attachments (e.g., spacers) described later in the present disclosure.

In some aspects, the first elongated plate 104a and the second elongated plate 104b may lie across the user's tongue 102, extend across the user's mouth, and rest against the commissures of the user's lips (where the upper and lower lip join). Stated another way, the first elongated plate 104a and the second elongated plate 104b may cross from side to side and extend beyond the user's tongue 102 to and across the lip commissures. The user's tongue 102 may be retained in the forward position by force from the lip commissures transferred through the first elongated plate 104a and the second elongated plate 104b to the user's tongue 102. Specifically, the proximal ends and the distal ends of the first elongated plate 104a and the second elongated plate 104b may be supported by the lip commissures, thereby preventing device 100 slipping inside the user's mouth.

The first elongated plate 104a and the second elongated plate 104b may be made of any material. In an exemplary aspect, the first elongated plate 104a and the second elongated plate 104b may be made of biodegradable single-use wood. The wood may include, but is not limited to, cedar wood, oak wood, birch etc. The wood may absorb water from the user's tongue 102, thereby creating an attachment to the user's tongue 102.

In further aspects, the first elongated plate 104a and the second elongated plate 104b may be made of plastic, metal, or any other material. In some aspects, the first elongated plate 104a and the second elongated plate 104b may be coated by using anti-microbial wax that inhibits the ability of microorganisms to grow on the surface of the first elongated plate 104a and the second elongated plate 104b. For example, the first elongated plate 104a and the second elongated plate 104b may be coated with beeswax. Such a coating may protect the user from any bacterial infection when the user places the device 100 over the user's tongue 102. Furthermore, the material of the first elongated plate 104a and/or the second elongated plate 104b may be non-toxic and sufficiently hydrophilic or frictional to remain in place on the user' tongue 102 for the desired duration of sleep. In further aspects, the first elongated plate 104a and/or the second elongated plate 104b may include at least one frictional or permeable side.

In addition, the first elongated plate 104a and the second elongated plate 104b may be of any shape. For example, the first elongated plate 104a and the second elongated plate 104b may be rectangular in shape. In further aspects, the first elongated plate 104a and the second elongated plate 104b may include one or more round or curved edges. For example, left and right edges of the first elongated plate 104a and the second elongated plate 104b may be curved. In other aspects, the first elongated plate 104a and the second elongated plate 104b may include all flat edges.

Furthermore, each of the first elongated plate 104a and the second elongated plate 104b may be of any dimension. In some aspects, the first elongated plate 104a dimensions may be the same as the second elongated plate 104b dimensions. In other aspects, the first elongated plate 104a dimensions may be different from the second elongated plate 104b dimensions. For example, a second elongated plate 104b length may be slightly smaller (e.g., smaller by 10-15%) than a first elongated plate 104a length. In some aspects, the first elongated plate 104a and/or the second elongated plate 104b may have a length in a range of three inches to eight inches, and a width in a range from a quarter of an inch to an inch and a half. In an exemplary aspect, the first elongated plate 104a and/or the second elongated plate 104b may be four-inch-long and one-inch-wide and one-sixteenth inch thick (approximately 10 cm×2 cm×2 mm). The dimensions described above are exemplary in nature and should not be construed as limiting.

The device 100 may further include one or more spacers that may be configured to attach or connect the first elongated plate 104a with the second elongated plate 104b, which prevents lateral and/or longitudinal slipping of the first elongated plate 104a and/or the second elongated plate 104b when the user uses the device 100. In some aspects, the spacers may be removably attached to the first elongated plate 104a and/or the second elongated plate 104b. In other aspects, the spacers may be permanently attached to the first elongated plate 104a and/or the second elongated plate 104b.

In an exemplary aspect, the spacers described above may include a first spacer 110a and a second spacer 110b (collectively referred as spacers 110). In some aspects, the first spacer 110a and the second spacer 110b may attach the first elongated plate 104a with the second elongated plate 104b such that an opening 112 may be formed between the first elongated plate 104a and the second elongated plate 104b, at a middle portion of the first elongated plate 104a and the second elongated plate 104b. Stated another way, the first spacer 110a and the second spacer 110b may attach the first elongated plate 104a and the second elongated plate 104b such that the second elongated plate 104b may be disposed at the predetermined distance "D" from the first elongated plate 104a. In some aspects, the opening 112 may be configured to receive and hold the user's tongue 102. In an exemplary aspect, the opening 112 may be approximately a quarter of an inch (about 5 mm) so that the second elongated plate 104b does not slip without exerting uncomfortable force, and placed snugly against the user's tongue 102.

In some aspects, the first spacer 110a may be located in proximity to the first proximal end 106a (associated with the first elongated plate 104a) and the second proximal end 108a (associated with the second elongated plate 104b). The first spacer 110a may be configured to attach the first proximal end 106a with the second proximal end 108a. Similarly, the second spacer 110b may be located in proximity to the first distal end 106b (associated with the first elongated plate 104a) and the second distal end 108b (associated with the second elongated plate 104b). In some aspects, the second spacer 110b may be configured to attach the first distal end 106b with the second distal end 108b.

In an exemplary aspect, the first spacer 110a and the second spacer 110b may surround the first elongated plate 104a and the second elongated plate 104b (on the proximal ends 106a, 108a and the distal ends 106b, 108b) to hold the first elongated plate 104a and the second elongated plate 104b such that the first elongated plate 104a and the second elongated plate 104b lay approximately a quarter of an inch (about 5 mm) apart to form the opening 112. The user's tongue 102 may be held by the first elongated plate 104a and the second elongated plate 104b (due to the first elongated plate 104a and the second elongated plate 104b absorbing moisture from the user's tongue 102) constrained with limited force by the first spacer 110a and the second spacer 110b near each end.

In some aspects, at least one of the first spacer 110a or the second spacer 110b may be made of a flexible material. For example, the first spacer 110a and the second spacer 110b may be made of an elastic material including, but not limited to, an elastic band or an elastic strap that may be covered with fabric, fabric sleeve, cotton twine, and/or the like. The material of the first spacer 110a and/or the second spacer 110b may be nontoxic, nonirritating, strong enough to hold the first elongated plate 104a and the second elongated plate 104b in place for the desired duration of sleep, and sufficiently small to avoid excessive discomfort. The elastic band or strap allows the user to adjust the opening 112 size according to user's tongue 102 thickness as well as to tightly hold the user's tongue 102 in the forward position. In some aspects, the elastic band or strap may be a loop of rubber (e.g., natural or synthetic rubber). The loop may be of any shape such as ring or oval shaped. The elastic band or strap may be of any thickness.

In further aspects, the elastic band (or the first spacer 110a) may loop around the first proximal end 106a and the second proximal end 108a (and may contact and/or attach with a first elongated plate 104a lower surface and a second elongated plate 104b upper surface) to attach the first elongated plate 104a with the second elongated plate 104b. Similarly, the elastic band (or the second spacer 110b) may loop around the first distal end 106b and the second distal end 108b (and may contact and/or attach with a first elongated plate 104a lower surface and a second elongated plate 104b upper surface) to attach the first elongated plate 104a with the second elongated plate 104b. The use of the elastic band (or any other flexible material) allows the user to adjust the opening 112 size according to the user's requirement.

In further aspects, each elastic band or strap (e.g., a portion of each elastic band) may be inserted between the first elongated plate 104a and the second elongated plate 104b to form the opening 112 between the first elongated plate 104a and the second elongated plate 104b, at the middle portion of the first elongated plate 104a and the second elongated plate 104b. For example, the elastic band (or the first spacer 110a) may be inserted between the first proximal end 106a and the second proximal end 108a, and the elastic band (or the second spacer 110b) may be inserted between the first distal end 106b and the second distal end 108b to form the opening 112 between the first elongated plate 104a and the second elongated plate 104b, at the middle portion of the first elongated plate 104a and the second elongated plate 104b.

In operation, the user may extend the user's tongue 102 from the mouth in a forward position, and clamp the user's tongue 102 position in the forward position using the device 100. Specifically, the user may insert the user's tongue 102 in the opening 112 described above. When the user inserts the user's tongue 102 in the opening 112, the first elongated plate 104a (e.g., the first elongated plate 104a upper surface) may contact a user's tongue 102 lower surface, and the second elongated plate 104b (e.g., the second elongated plate 104b lower surface) may contact a user's tongue 102 upper surface. Once the user's tongue 102 is inserted in the opening 112, the first spacer 110a and the second spacer 110b may clamp/hold the user's tongue 102 in the forward position. The user may further adjust the opening 112 size using the first spacer 110a and/or the second spacer 110b, as per the user's tongue thickness. Once the user's tongue 102 is securely held between the first elongated plate 104a and the second elongated plate 104b, the user may conveniently sleep without experiencing any discomfort from snoring, sleep apnea, breathlessness, and/or the like.

Figure 2:
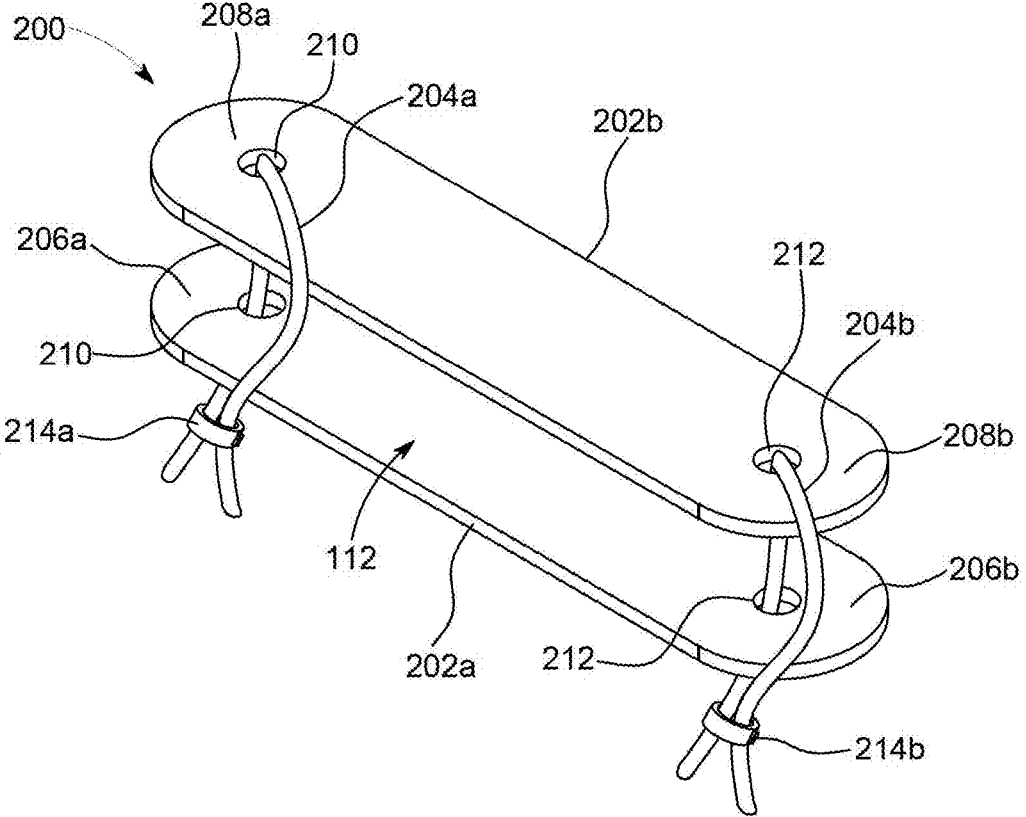
FIG. 2 depicts a second embodiment of a tongue positioning device in accordance with the present disclosure.

FIG. 2 depicts a second embodiment of a tongue positioning device 200 in accordance with the present disclosure. The tongue positioning device 200 (or device 200) may be configured to hold the user's tongue 102 similar to the device 100 described above.

In some aspects, the device 200 may include a first elongated plate 202a and a second elongated plate 202b. The second elongated plate 202b may be placed above the first elongated plate 202a. The first elongated plate 202a may be same as the first elongated plate 104a, and the second elongated plate 202b may be same as the second elongated plate 104b described above in conjunction with FIG. 1. In addition, the device 200 may include a first spacer 204a and a second spacer 204b, which may be configured to attach the first elongated plate 202a and the second elongated plate 202b. The first spacer 204a may be same as the first spacer 110a, and the second spacer 204b may be same as the second spacer 110b described above.

The first elongated plate 202a may include a first proximal end 206a and a first distal end 206b. Similarly, the second elongated plate 202b may include a second proximal end 208a and a second distal end 208b. In some aspects, the first proximal end 206a and the second proximal end 208a may include a first through-holes 210, and the first distal end 206b and the second distal end 208b may include a second through-holes 212. In some aspects, the first spacer 204a and the second spacer 204b may be configured to pass through the first through-holes 210 and the second through-holes 212 respectively to attach the first elongated plate 202a with the second elongated plate 202b, and allow the user to adjust the opening 112 size, as described above. In some aspects, the size of the first through-holes 210 and the second through-holes 212 may correspond to or be equivalent to the width/thickness of the first spacer 204a and the second spacer 204b.

In some aspects, the device 200 may further include a first stopper 214a and a second stopper 214b. The first stopper 214a may be associated with the first spacer 204a and the second stopper 214b may be associated with the second spacer 204b. In some aspects, the first stopper 214a and the second stopper 214b may be cord lock stoppers that may be made of any material such as plastic, and may be of any size. The first stopper 214a may lock the first spacer 204a and prevent detachment of the second proximal end 208a from the first proximal end 206a, and allow the user to adjust the opening 112 size (via the first spacer 204a and the first stopper 214a). Similarly, the second stopper 214b may lock the second spacer 204b and prevent detachment of the second distal end 208b from the first distal end 206b, and allow the user to adjust the opening 112 size (via the second spacer 204b and the second stopper 214b).

Remaining features of the device 200 are similar to the features of the device 100, and hence are not described again here for the sake of simplicity and conciseness.

Figure 3:
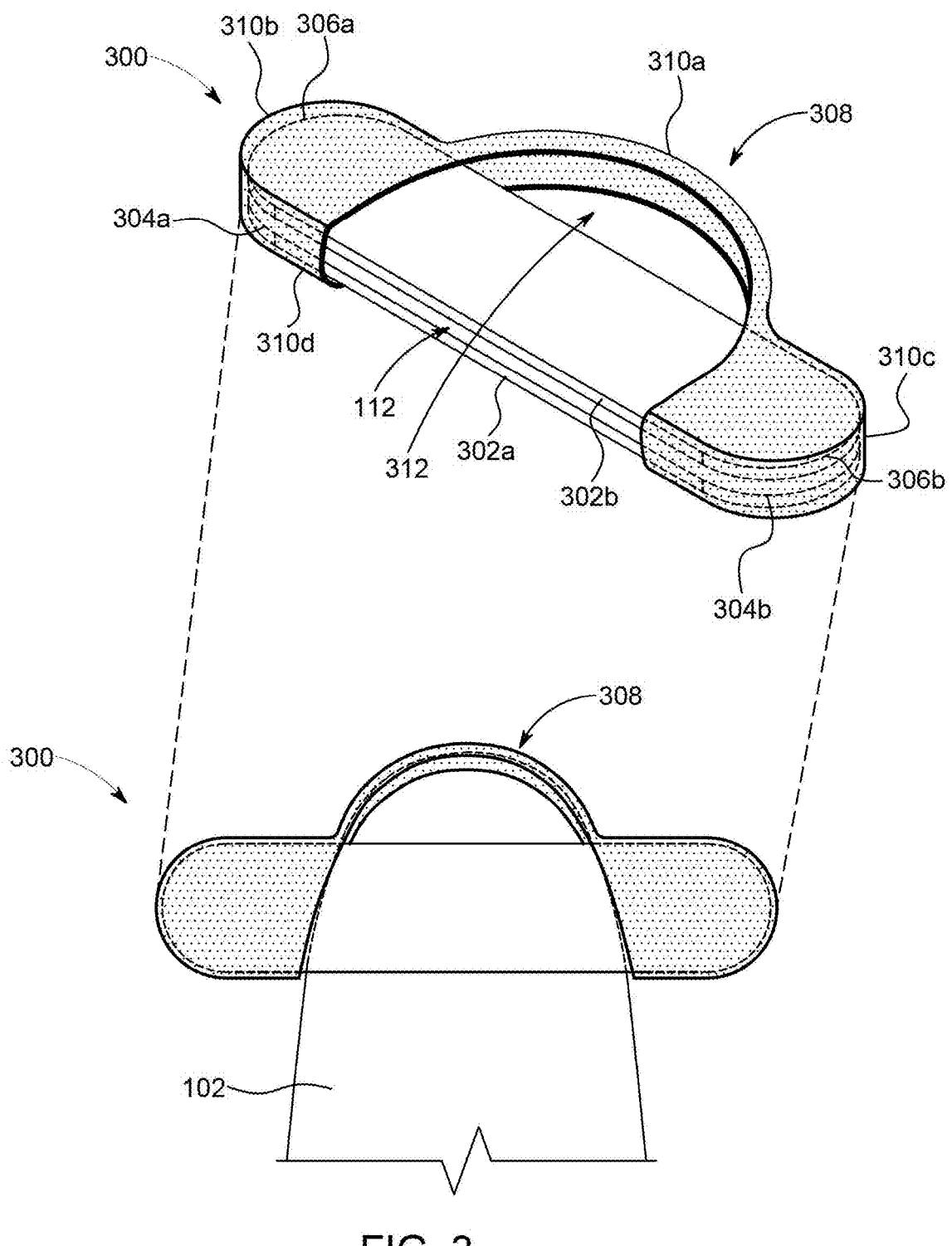
FIG. 3 depicts a third embodiment of a tongue positioning device in accordance with the present disclosure.

FIG. 3 depicts a third embodiment of a tongue positioning device 300 in accordance with the present disclosure. The tongue positioning device 300 (or device 300) may be similar to the device 100 and/or the device 200 described above.

In some aspects, the device 300 may include a first elongated plate 302a and a second elongated plate 302b. The second elongated plate 302b may be placed above the first elongated plate 302a. The first elongated plate 302a may be same as the first elongated plate 104a, and the second elongated plate 302b may be same as the second elongated plate 104b described above in conjunction with FIG. 1. The first elongated plate 302a may include a first proximal end 304a and a first distal end 304b. Similarly, the second elongated plate 302b may include a second proximal end 306a and a second distal end 306b. In further aspects, the device 300 may include a first spacer and a second spacer (not shown in FIG. 3), which may be same as the first spacer 204a or 110a and the second spacer 204b or 110b described above.

In some aspects, the device 300 may further include a cover 308 configured to cover or enclose fully or partially the first elongated plate 302a, the second elongated plate 302b, the first spacer and the second spacer. The cover 308 may be further configured to cover the tip portion or the outermost portion of the user's tongue 102 (to keep the user's tongue 102 clean) when the user wears the device 300 to hold the user's tongue 102 in the forward or extended position. In addition, the cover 308 may be configured to bind/attach the first elongated plate 302a and the second elongated plate 302b together.

The cover 308 may be made of any material. For example, the cover 308 may be made of flexible material such as latex, silicone, and/or the like. In other aspects, the cover 308 may be made of plastic, metal, and/or the like. In some aspects, the cover 308 may be flexible. In other aspects, the cover 308 may be rigid. In some aspects, the cover 308 may be removably placed on the first elongated plate 302a and the second elongated plate 302b. In other aspects, the cover 308 may be fixed to at least one of the first elongated plate 302a or the second elongated plate 302b (e.g., attached at one end of the first elongated plate 302a and/or the second elongated plate 302b).

The cover 308 may have a design/shape such that the user may conveniently place the cover 308 over the device components to enclosure them, while at the same time, the device 300 with the cover 308 may be comfortable for the user to use/wear when the user may be sleeping with the device 300 placed on the user's tongue 102. In an exemplary aspect, the cover 308 may have a front portion 310a, a left side portion 310b, a right side portion 310c, and a back portion 310d. In some aspects, the front portion 310a, the left side portion 310b, and the right side portion 310c may be closed. In further aspects, the back portion 310d may include an opening 312 (or cavity) that may be configured to receive the user's tongue 102 to cover the user's tongue 102 tip portion and user's tongue 102 side portions. When the user uses the cover 308, the front portion 310a may be in proximity to the user's tongue 102 tip portion, and the left side portion 310b and the right side portion 310c may be in proximity to the user's tongue 102 side portions.

In some aspects, the left side portion 310b may be configured to cover/enclose and hold the first proximal end 304a and the second proximal end 306a. For example, the left side portion 310b may fit snugly over the first proximal end 304a and the second proximal end 306a, to hold the first proximal end 304a and the second proximal end 306a. In addition, the left side portion 310b may be configured to cover/enclose the first spacer that may be used to attach the first and second proximal ends 304a, 306a. In further aspects, the right side portion 310c may be configured to cover/enclose and hold the first distal end 304b and the second distal end 306b. For example, the right side portion 310c may fit snugly over the first distal end 304b and the second distal end 306b, to hold the first proximal end 304a and the second proximal end 306a. In addition, the right side portion 310c may be configured to cover/enclose the second spacer that may be used to attach the first and second distal ends 304b, 306b.

In further aspects, the front portion 310a may be configured to cover middle portions of the first elongated plate 302a and the second elongated plate 302b. The middle portion may be disposed between the proximal ends 304a, 306a and the distal ends 304b, 306b. In some aspects, the front portion 310a may fully cover the middle portions of the first elongated plate 302a and the second elongated plate 302b. In other aspects, the front portion 310a may partially cover the middle portions of the first elongated plate 302a and the second elongated plate 302b. In alternative aspects, the front portion 310a may not cover the middle portions of the first elongated plate 302a and the second elongated plate 302b.

In some aspects, the front portion 310a may be arc-shaped (or rounded/dome shaped, which may correspond to the shape of a tip or outermost portion of a standard-sized tongue), which enables effective covering of the user's tongue 102 without causing any inconvenience to the user while using the device 300. In some aspects, the arc may be located throughout a front portion 310a length. In other aspects, the arc may be located at a portion of the front portion 310a length. Due to this arc-shape, the user may not be required to apply pressure on the cover 308 to wear the cover 308. In some aspects, the front portion 310a may conform to the shape of the user's tongue 102 outermost portion to effectively cover the user's tongue 102 from its tip portion.

In operation, the user may insert the user's tongue 102 in the opening 112, as described in conjunction with FIG. 1. Once the user's tongue 102 is inserted, the user may place the cover 308 to cover the first elongated plate 302a, the second elongated plate 302b, the first spacer, and the second spacer in the manner described above. In another aspect, the cover 308 may already be placed on the device 300 when the user inserts the user's tongue 102 in the opening 112.

Remaining features of the device 300 are same as the features of the device 100, and hence are not described again here for the sake of simplicity and conciseness.

Figure 4:
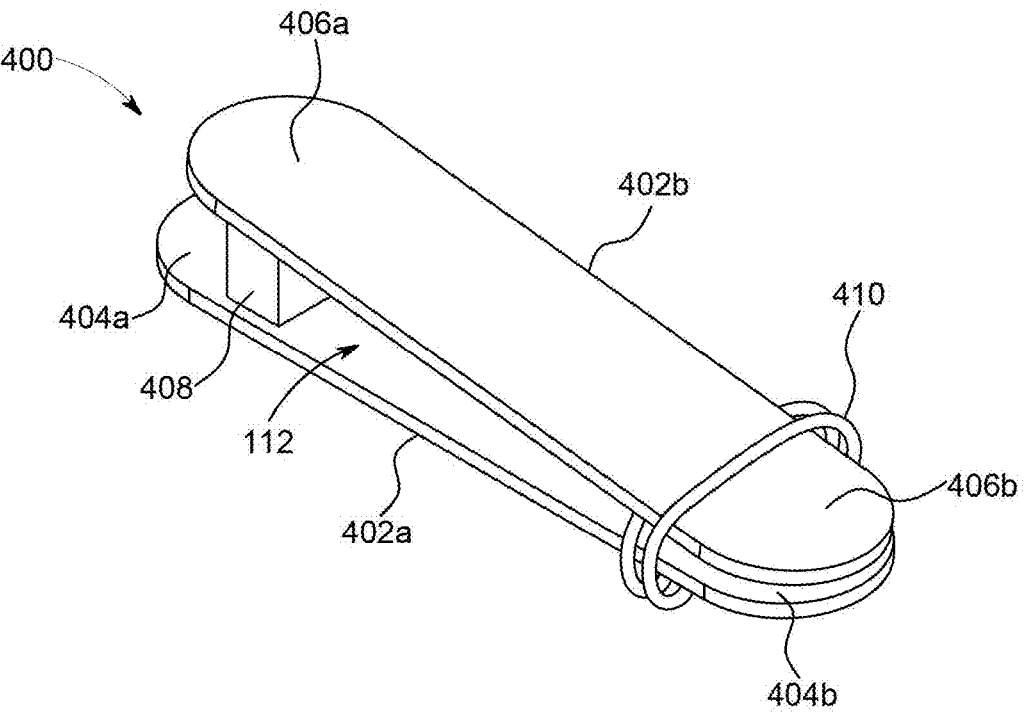
FIG. 4 depicts a fourth embodiment of a tongue positioning device in accordance with the present disclosure.

FIG. 4 depicts a fourth embodiment of a tongue position-ing device 400 in accordance with the present disclosure. The tongue positioning device 400 (or device 400) may be similar to the device 100 and/or the device 200 described above.

In some aspects, the device 400 may include a first elongated plate 402a and a second elongated plate 402b. The second elongated plate 402b may be placed above the first elongated plate 402a. The first elongated plate 402a may be same as the first elongated plate 104a, and the second elongated plate 402b may be same as the second elongated plate 104b described above in conjunction with FIG. 1. The first elongated plate 402a may include a first proximal end 404a and a first distal end 404b. Similarly, the second elongated plate 402b may include a second proximal end 406a and a second distal end 406b.

In further aspects, the device 400 may include a first spacer 408 and a second spacer 410. The second spacer 410 may be same as the first spacer 204a or 110a or the second spacer 204b or 110b described above. The second spacer 410 may be configured to attach the first distal end 404b and the second distal end 406b (e.g., removably attach the first distal end 404b and the second distal end 406b).

In some aspects, the first spacer 408 may be configured to be disposed/placed between the first elongated plate 402a and the second elongated plate 402b so that there exists a gap (same as the opening 112) between the first elongated plate 402a and the second elongated plate 402b, to enable the device 400 to receive the user's tongue 102. The first spacer 408 may be disposed in proximity to the first proxi-mal end 404a and the second proximal end 406a, and may be configured to attach the first proximal end 404a and the second proximal end 406a. In an exemplary aspect, the first spacer 408 may be a block (e.g., a rectangular or a square block) that may be attached (e.g., permanently attached) to the first elongated plate 402a and the second elongated plate 402b. As an example, the block may be placed between first elongated plate 402a and the second elongated plate 402b to attach the first elongated plate 402a with the second elongated plate 402b. The block may be made of a flexible material such as rubber. In some aspects, the block may be an elastic block. The block may be of any size. In some aspects, the block width may correspond to the width of the first elongated plate 402a and the second elongated plate 402b.

In operation, the user may press the first proximal end 404a and the second proximal end 406a against each other. Pressing of the first proximal end 404a and the second proximal end 406a against each other may increase the distance between the first distal end 404b and the second distal end 406b. The user may then insert the user's tongue 102 between the first elongated plate 402a and the second elongated plate 402b (e.g., in the opening 112 at the middle portion of the first elongated plate 402a and the second elongated plate 402b). Once the user's tongue 102 may be inserted, the user may attach the first distal end 404b and the second distal end 406b using the second spacer 410, in the manner described above.

Figure 5:
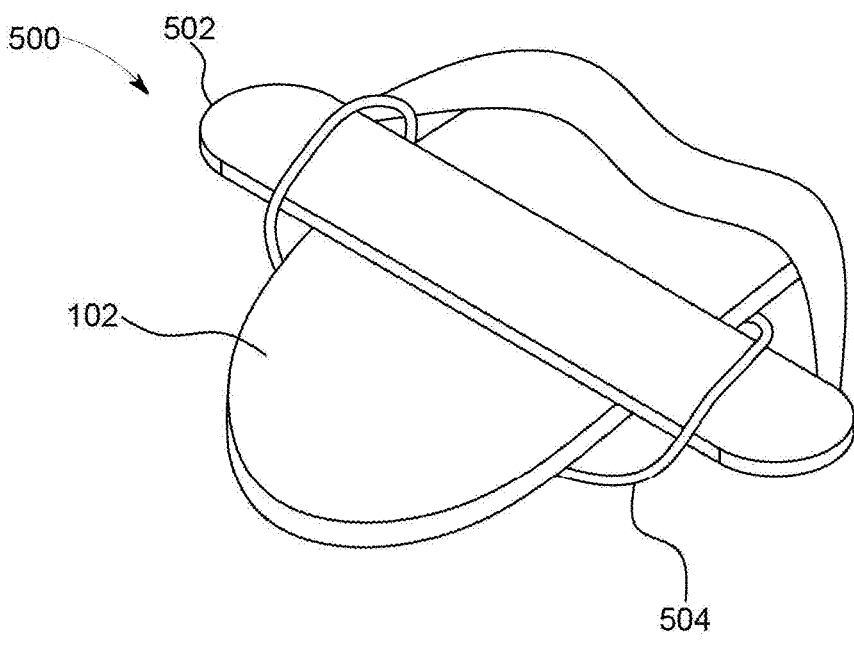
FIG. 5 depicts a fifth embodiment of a tongue positioning device in accordance with the present disclosure.

FIG. 5 depicts a fifth embodiment of a tongue positioning device 500 in accordance with the present disclosure. The tongue positioning device 500 (or device 500) may be different from the devices described above, and may include a single elongated plate 502 (or plate 502) instead of two elongated plates described above. The plate 502 may be same as the first elongated plate 104a or the second elon-gated plate 104b described above. The plate 502 may be placed above the user's tongue 102 in the same manner as the second elongated plate 104b is placed above the user's tongue 102.

In some aspects, the device 500 may further include a holding mechanism 504 that may be configured to hold the plate 502 on the user's tongue 102. In some aspects, the holding mechanism 504 may be an elastic band or strap (similar to the first spacer 110a and the second spacer 110b). The elastic band may loop around the plate 502 and the user's tongue 102 such that the device 500 holds the user's tongue 102 in the forward/extended direction.

Figure 6:
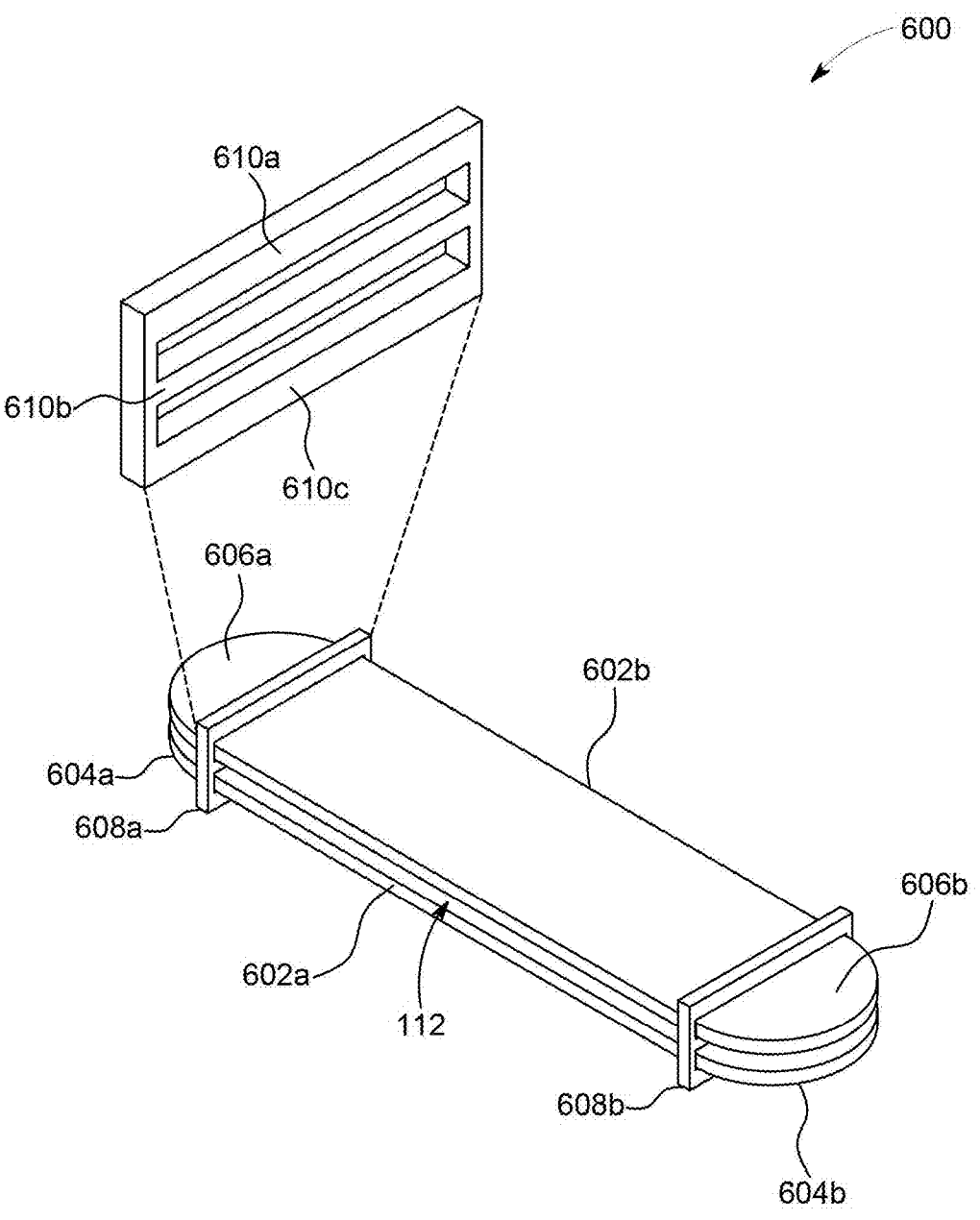
FIG. 6 depicts a sixth embodiment of a tongue positioning device in accordance with the present disclosure.

FIG. 6 depicts a sixth embodiment of a tongue positioning device 600 in accordance with the present disclosure. The tongue positioning device 600 (or device 600) may be similar to the device 100 and/or the device 200 described above.

In some aspects, the device 600 may include a first elongated plate 602a and a second elongated plate 602b. The second elongated plate 602b may be placed above the first elongated plate 602a. The first elongated plate 602a may be same as the first elongated plate 104a, and the second elongated plate 602b may be same as the second elongated plate 104b described above in conjunction with FIG. 1. The first elongated plate 602a may include a first proximal end 604a and a first distal end 604b. Similarly, the second elongated plate 602b may include a second proximal end 606a and a second distal end 606b.

In further aspects, the device 600 may include a first spacer 608a and a second spacer 608b. In some aspects, the first spacer 608a may be same as the second spacer 608b. In an exemplary aspect, the first spacer 608a and the second spacer 608b may be buckle connectors that may be config-ured to connect the first elongated plate 602a and the second elongated plate 602b. For example, the first spacer 608a may attach/connect the first proximal end 604a and the second proximal end 606a. Similarly, the second spacer 608b may attach/connect the first distal end 604b and the second distal end 606b.

In an exemplary aspect, the first spacer 608a and the second spacer 608b may surround the first elongated plate 602a and the second elongated plate 602b (on the proximal ends 604a, 606a and the distal ends 604b, 606b) to hold the first elongated plate 602a and the second elongated plate 602b together such that the first elongated plate 602a and the second elongated plate 602b lay to form the opening 112. Stated another way, the first spacer 608a and the second spacer 608b may be placed around and between first elon-gated plate 602a and the second elongated plate 602b to attach the first elongated plate 602a with the second elon-gated plate 602b and to create a gap or the opening 112 between the first elongated plate 602a and the second elongated plate 602b. In some aspects, at least one of the first spacer 608*a* or the second spacer 608*b* may be made of flexible material such as rubber, to effectively hold the user's tongue 102.

In an exemplary aspect, the buckle type connector (or the first spacer 608*a* and the second spacer 608*b*) may be a solid connector that may include a first plate 610*a*, a second plate 610*b*, and a third plate 610*c* that may be disposed parallel to each other. The first plate 610*a*, the second plate 610*b*, and the third plate 610*c* may form a unified buckle connector. The first plate 610*a* and the third plate 610*c* may surround the first elongated plate 602*a* and the second elongated plate 602*b* (e.g., a top surface of the second elongated plate 602*b* and a bottom surface of the first elongated plate 602*a*). Stated another way, the first plate 610*a* and the third plate 610*c* may contact exterior surfaces of the first elongated plate 602*a* and the second elongated plate 602*b*. The second plate 610*b* may be disposed between the first elongated plate 602*a* and the second elongated plate 602*b* to form the opening 112. The second plate 610*b* may contact the bottom surface of the second elongated plate 602*b* and the top surface of the first elongated plate 602*a*. Stated another way, the second plate 610*b* may contact interior surfaces of the first elongated plate 602*a* and the second elongated plate 602*b*.

Remaining structural details of the device 600 are same as the structural details of the device 100/200, and hence are not described again here for the sake of simplicity and conciseness.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a feature, structure, or characteristic is described in connection with an embodiment, one skilled in the art will recognize such feature, structure, or characteristic in connection with other embodiments whether or not explicitly described.

It should also be understood that the word "example" as used herein is intended to be non-exclusionary and non-limiting in nature. More particularly, the word "example" as used herein indicates one among several examples, and it should be understood that no undue emphasis or preference is being directed to the particular example being described.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating various embodiments and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc., should be read to recite one or more of the indicated elements unless a claim recites an explicit limitation to the contrary. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A device configured to hold a user's tongue, the device comprising:
   a first elongated plate having a first proximal end and a first distal end;
   a second elongated plate placed above the first elongated plate, wherein:
   the second elongated plate comprises a second proximal end and a second distal end,
   the first elongated plate is configured to directly attach to a bottom surface of the user's tongue and the second elongated plate is configured to directly attach to a surface of the user's tongue, and
   the first elongated plate and the second elongated plate are made of wood that is configured to absorb water from the user's tongue to thereby create an attachment to the user's tongue;
   a first spacer configured to attach the first proximal end with the second proximal end; and
   a second spacer configured to attach the first distal end with the second distal end, wherein:
   the first spacer and the second spacer are further configured to form an opening between the first elongated plate and the second elongated plate at a middle portion of the first elongated plate and the second elongated plate, wherein at least a portion of the first spacer and the second spacer is located between the first elongated plate and the second elongated plate to form the opening between the first elongated plate and the second elongated plate,
   the opening is configured to receive the user's tongue, and
   at least one of the first spacer or the second spacer is made of a flexible material.

2. The device of claim 1 further comprising a cover configured to cover the first elongated plate, the second elongated plate, the first spacer and the second spacer when the device is in use to hold the user's tongue, wherein the cover is configured to partially cover the first elongated plate and the second elongated plate when the device is in use to hold the user's tongue.

3. The device of claim 2, wherein the cover comprises a front portion, a left side portion, a right side portion, and a back portion, and wherein the back portion comprises an opening to receive the user's tongue.

4. The device of claim 3, wherein the left side portion is configured to cover the first proximal end and the second proximal end, wherein the right side portion is configured to cover the first distal end and the second distal end, and wherein the front portion is configured to cover a tip portion of the user's tongue.

5. The device of claim 3, wherein the front portion is arc-shaped.

6. The device of claim 2, wherein the cover is made of flexible material.

7. The device of claim 1, wherein the second spacer is an elastic block.

8. The device of claim 7, wherein the elastic block is placed between the first distal end and the second distal end to attach the first distal end and the second distal end.

9. The device of claim 1, wherein the first spacer is an elastic band.

10. The device of claim 1, wherein the second spacer is an elastic band.

11. The device of claim 1, wherein the first spacer is configured to surround the first proximal end and the second proximal end to attach the first proximal end with the second proximal end, and wherein the second spacer is configured to surround the first distal end and the second distal end to attach the first distal end with the second distal end.

12. The device of claim 1, wherein the first proximal end and the second proximal end comprise first through-holes, wherein the first distal end and the second distal end comprise second through-holes, and wherein the first spacer and the second spacer are configured to pass through the first through-holes and the second through-holes, respectively, to attach the first elongated plate with the second elongated plate.

13. The device of claim 1, wherein the first elongated plate and the second elongated plate are coated with anti-microbial wax.

14. The device of claim 1, wherein the first elongated plate and the second elongated plate are configured to be placed across the user's tongue and rest against commissures of user's lips.

15. The device of claim 1, wherein dimensions of the first elongated plate are different from dimensions of the second elongated plate.

16. The device of claim 1, wherein the first spacer and the second spacer are buckle connectors, and wherein each buckle connector comprises a first plate, a second plate, and a third plate disposed parallel to each other.

17. A device configured to hold a user's tongue, the device comprising:

a first elongated plate having a first proximal end and a first distal end;

a second elongated plate placed above the first elongated plate, wherein:

the second elongated plate comprises a second proximal end and a second distal end, the first elongated plate is configured to directly attach to a bottom surface of the user's tongue and the second elongated plate is configured to directly attach to a top surface of the user's tongue, and the first elongated plate and the second elongated plate are made of wood that is configured to absorb water from the user's tongue to thereby create an attachment to the user's tongue;

a first spacer configured to attach the first proximal end with the second proximal end; and a second spacer configured to attach the first distal end with the second distal end, wherein:

the first spacer and the second spacer are further configured to form an opening between the first elongated plate and the second elongated plate at a middle portion of the first elongated plate and the second elongated plate, wherein at least a portion of the first spacer and the second spacer is located between the first elongated plate and the second elongated plate to form the opening between the first elongated plate and the second elongated plate, the opening is configured to receive the user's tongue, and the first elongated plate and the second elongated plate are coated with anti-microbial wax.

18. The device of claim 17, wherein each of the first spacer and the second spacer is an elastic band.

19. The device of claim 17, wherein the second spacer is an elastic block, and wherein the elastic block is placed between the first distal end and the second distal end to attach the first distal end and the second distal end.

20. A device configured to hold a user's tongue, the device comprising:

a first elongated plate having a first proximal end and a first distal end;

a second elongated plate placed above the first elongated plate, wherein:

the second elongated plate comprises a second proximal end and a second distal end, the first elongated plate is configured to directly attach to a bottom surface of the user's tongue and the second elongated plate is configured to directly attach to a top surface of the user's tongue, and the first elongated plate and the second elongated plate are made of wood that is configured to absorb water from the user's tongue to thereby create an attachment to the user's tongue;

a first spacer configured to attach the first proximal end with the second proximal end;

a second spacer configured to attach the first distal end with the second distal end, wherein:

the first spacer and the second spacer are further configured to form an opening between the first elongated plate and the second elongated plate at a middle portion of the first elongated plate and the second elongated plate, wherein at least a portion of the first spacer and the second spacer is located between the first elongated plate and the second elongated plate to form the opening between the first elongated plate and the second elongated plate, and the opening is configured to receive the user's tongue; and a cover configured to cover the first elongated plate, the second elongated plate, the first spacer and the second spacer when the device is in use to hold the user's tongue.

* * * * *